(12) United States Patent
Irion et al.

(10) Patent No.: US 9,066,656 B2
(45) Date of Patent: Jun. 30, 2015

(54) DEFLECTABLE AUTOCLAVABLE ENDOSCOPE

(75) Inventors: Klaus M. Irion, Emmingen-Liptingen (DE); Thomas Ruegg, Vancouver (CA)

(73) Assignee: KARL STORZ GMBH & CO. KG (DE)

( * ) Notice: Subject to any disclaimer, the term of this patent is extended or adjusted under 35 U.S.C. 154(b) by 1590 days.

(21) Appl. No.: 12/052,225

(22) Filed: Mar. 20, 2008

(65) Prior Publication Data

US 2008/0234547 A1 Sep. 25, 2008

(30) Foreign Application Priority Data

Mar. 20, 2007 (DE) .......................... 10 2007 014 739

(51) Int. Cl.
| A61B 1/00 | (2006.01) |
| A61B 1/04 | (2006.01) |
| A61M 25/00 | (2006.01) |
| A61B 1/005 | (2006.01) |
| A61B 1/01 | (2006.01) |
| A61B 1/12 | (2006.01) |

(52) U.S. Cl.
CPC ............ *A61B 1/0056* (2013.01); *A61B 1/00071* (2013.01); *A61B 1/00105* (2013.01); *A61B 1/00147* (2013.01); *A61B 1/00183* (2013.01); *A61B 1/01* (2013.01); *A61B 1/121* (2013.01)

(58) Field of Classification Search
CPC ........... A61B 1/00071; A61B 1/00078; A61B 1/00089; A61B 1/00101; A61B 1/00135; A61B 1/0014; A61B 1/00154; A61B 1/0051; A61B 1/0055; A61B 1/0056; A61B 1/0057; A61B 1/0058; A61B 1/008; A61B 1/01; A61B 1/313; A61B 1/3132

USPC .................. 600/104, 106, 114, 139–152, 107, 600/129–131; 604/95.01–95.05, 523–528

See application file for complete search history.

(56) References Cited

U.S. PATENT DOCUMENTS

| 4,688,554 | A | * | 8/1987 | Habib ........................... 600/114 |
| 5,318,008 | A | * | 6/1994 | Bullard ......................... 600/139 |
| 5,402,768 | A | | 4/1995 | Adair |
| 5,630,782 | A | | 5/1997 | Adair |
| 5,976,075 | A | | 11/1999 | Beane et al. |
| 6,464,631 | B1 | | 10/2002 | Girke et al. |
| 6,569,085 | B2 | | 5/2003 | Kortenbach et al. |
| 6,605,036 | B1 | * | 8/2003 | Wild ............................. 600/131 |
| 2006/0217694 | A1 | * | 9/2006 | Chin et al. ...................... 606/15 |

FOREIGN PATENT DOCUMENTS

| DE | 4222271 A1 | 1/1994 |
| DE | 4442185 A1 | 5/1996 |
| DE | 19955229 C1 | 8/2001 |

OTHER PUBLICATIONS

European Search Report; EP 08 00 5256; Jan. 26, 2009; 5 pages.

* cited by examiner

*Primary Examiner* — Ryan Henderson
(74) *Attorney, Agent, or Firm* — Whitmyer IP Group LLC

(57) ABSTRACT

An endoscope has a shaft housing a lighting and an image transmission system and said endoscope being designed to be autoclavable. The shaft has a distal end portion which is made deflectable. An outer part is provided which is attached to said shaft. The outer part has a deflector mechanism for deflecting said deflectable distal end portion of said shaft and said outer part can be attached to said shaft by being releasably mounted laterally onto said shaft.

20 Claims, 3 Drawing Sheets

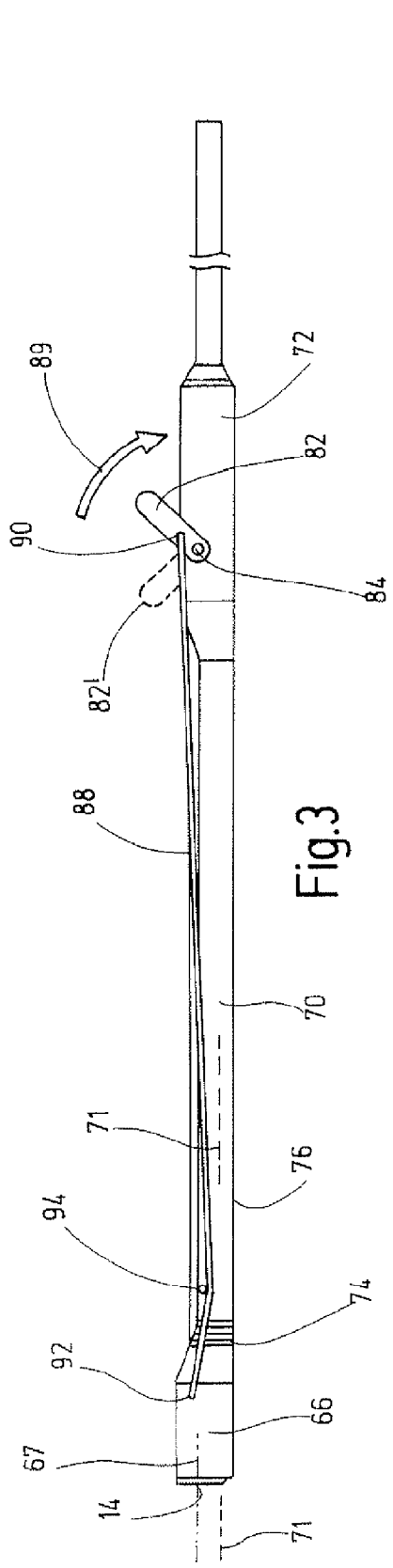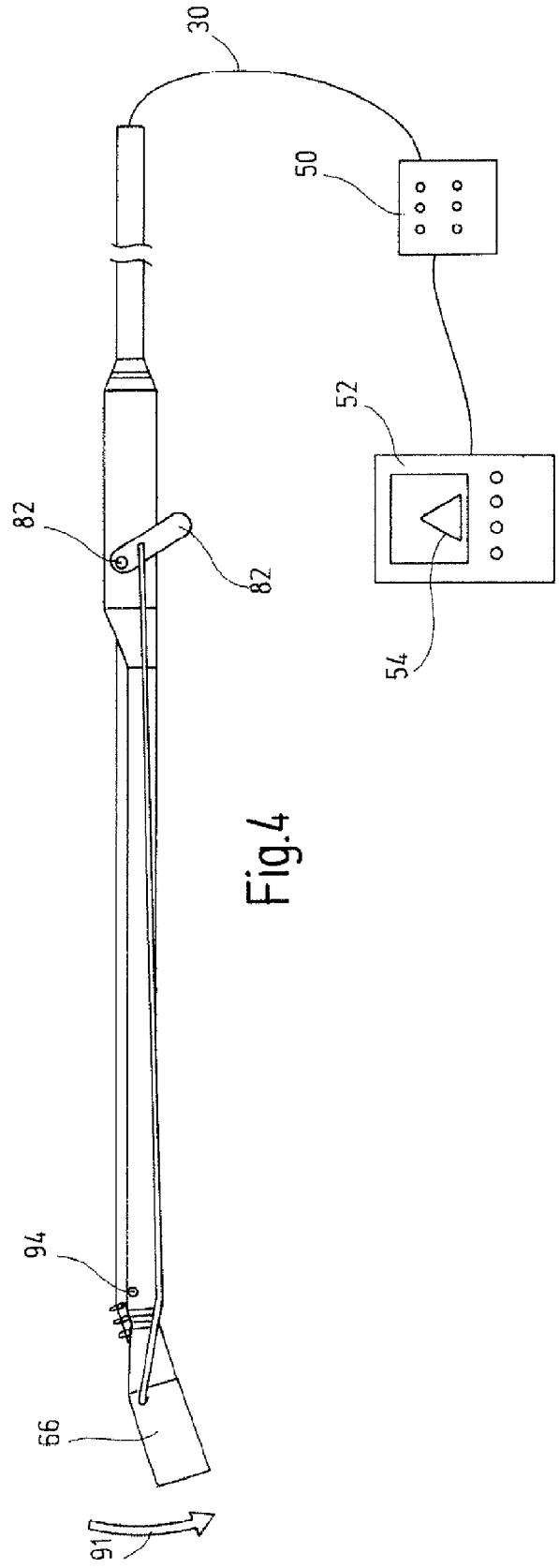

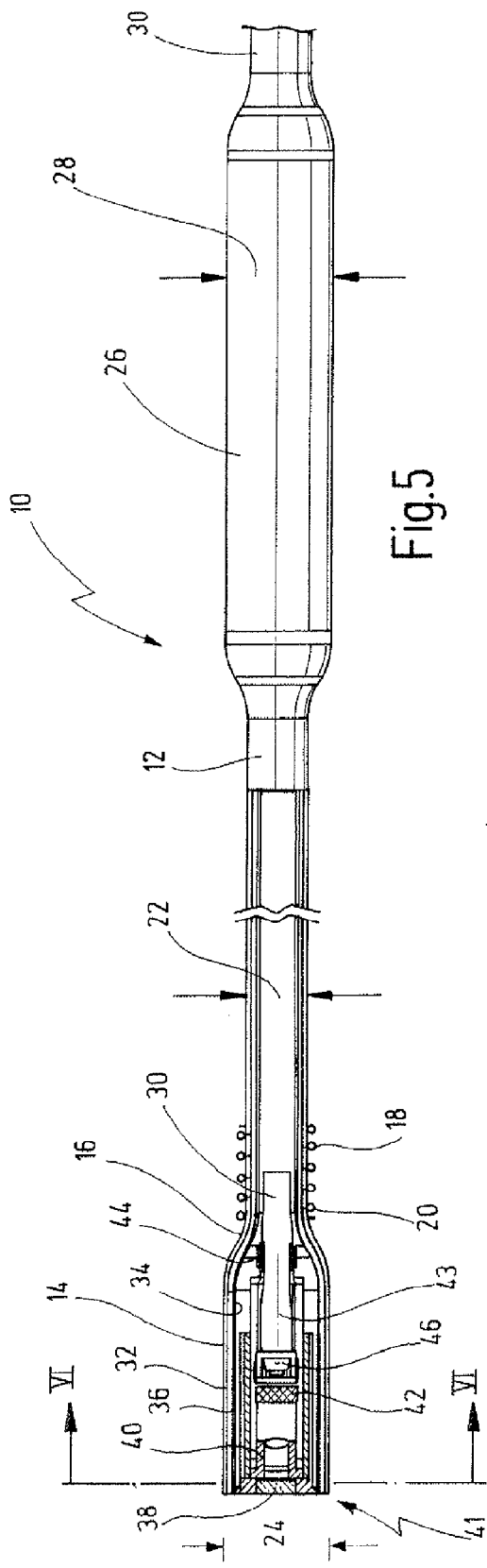

DEFLECTABLE AUTOCLAVABLE ENDOSCOPE

BACKGROUND OF THE INVENTION

The invention relates to an endoscope with a shaft that houses a lighting and image transmission system, the endoscope being designed to be autoclavable.

Endoscopes of this kind are widely known and are used in minimally invasive surgery. In rigid endoscopes, the shaft is made of a stiff material, in most cases medical-grade steel. In flexible endoscopes, the shaft, at least in the flexible area, is made of a pliant plastic material.

The shaft of the endoscope comes into direct contact with the tissue during use and is thus exposed to contamination. For economic reasons, it is of advantage to be able to use such endoscopes more than once.

For this purpose, the endoscopes initially have to be cleaned after use and thereafter have to be sterilized, this usually being done by an autoclaving process.

In autoclaving, the endoscope is exposed to relatively high temperatures. In what is called flash autoclaving, it is exposed to temperatures of over 134° to 165° C. In addition, chemicals, for example peroxide-containing chemicals, are sometimes added to the autoclave, in order to achieve absolute sterility.

As minimally invasive surgery is becoming increasingly more common, these cycles are being carried out several times a day, with the result that such endoscopes are exposed to considerable stresses, which they have to be able to withstand over a long period.

In rigid endoscopes, this can be achieved by using suitable metals.

In flexible endoscopes, this cannot be achieved with any great certainty, since the flexible materials, mostly plastics, do not withstand these harsh conditions over the long term. However, the flexibility allows the operator much greater viewing ranges, specifically since the distal end can be curved, resulting not only in a straight-ahead view but also in an all-round lateral view.

In rigid endoscopes, the distal end has suitably bevelled lenses in order to permit not only a straight-ahead view (0° view) but also angled oblique views of up to 45°.

There is a need, however, for autoclavable endoscopes that permit a flexible viewing direction.

U.S. Pat. No. 5,402,768 discloses designing the shaft of an endoscope in such a way that an inner shaft core houses the optical elements of the image transmission system. These can be conventionally rigid glass lenses or, in more modern constructions, imaging elements in the form of semiconductor image sensors (CCD, CMOS). The incident image is reflected via a lens onto the semiconductor image sensor and is converted there into electrical signals that are routed through cables in the inside of the shaft to the proximal end of the endoscope. These signals are then processed and are in most cases displayed as an image on a monitor. Since the structural units of a semiconductor image sensor are getting ever smaller, they can be used in particular in flexible endoscopes, since a curvature of the shaft does not impair these small structural parts.

However, the problem of autoclaving arises here.

In U.S. Pat. No. 5,402,768, this problem is remedied by a tubular cover being pushed over the inner core of the shaft so as to completely cover the latter and seal it hermetically at the distal end. At the proximal end, the tube even has bellows-like folds that can be pulled for protection over the whole proximal end area of the shaft, and thus also of the endoscope.

As a result, the shaft itself no longer comes into contact with the tissue during an intervention, only the outer sleeve that has been pushed over it.

After one use, the sleeve is removed again and discarded.

In one embodiment, control wires are integrated in the outer sleeve and can be used to curve the assembly of flexible shaft and outer flexible sleeve.

This endoscope is awkward to handle, since the sterile tube has to be pushed onto the long thin shaft of the endoscope before each use, and this requires a certain skill. It is not possible to exclude the possibility of the shaft being contaminated during these preparatory manoeuvres.

The risk of contamination is much greater when, after use, the tube is removed again from the shaft and discarded. It is therefore necessary for the inner core, which contains the image transmission system, to be sterilized by disinfecting liquids. However, these procedures are very time-consuming and, after a large number of uses, there is the possibility of the aggressive chemical substances passing through the plastic wall of the core and penetrating into the interior of the core.

The object of the present invention is therefore to make available an autoclavable endoscope that is deflectable and is easy to handle.

SUMMARY OF THE INVENTION

According to the invention this object is achieved by an endoscope, comprising a shaft housing a lighting and an image system, said endoscope being designed to be autoclavable, said shaft having a distal end portion which is made deflectable. An outer part is provided, which is attached to the shaft. Said outer part has a deflector mechanism for deflecting said deflectable distal end portion of said shaft, and said outer part can be attached to said shaft by being releasably mounted laterally onto said shaft.

These measures now afford a number of advantages.

The sensitive structural elements, such as the image transmission system and also the lighting system, can be housed in a hermetically sealed manner in the shaft.

For the deflection, a separate part is applied, namely the outer part, which comprises the deflector mechanism. Since the outer part can be attached laterally onto the shaft or, conversely, the shaft can be inserted laterally into the outer part, handling is easy. It can be done, for example, by simple insertion, clipping or a snap-fit. By providing a distally deflectable end portion of the shaft, only a certain area of the shaft has to have a degree of flexibility in order to permit this deflection. This can also be achieved with relatively stiff or metal materials, for example by bellows-like formations or thinning of the material, such that the shaft does not have to be made entirely from a flexible material. In other words, the shaft can be made entirely of metal, as before, and simply has to show the flexibility at the deflection site in the distal area. The outer part contains the deflector mechanism via which the distal end portion of the shaft can be deflected after the outer part has been mounted laterally on the shaft, or vice versa.

A further advantage is that, without the outer part, the endoscope can be used as a "classical" rigid endoscope, i.e. the outer part is then not applied at all, and it is applied only when deflection is required. This can be done easily and quickly, specifically by the outer part being simply mounted laterally onto the shaft.

This can also be done in the course of a surgery and does not necessarily have to be done prior to a surgery, such that the outer part does not have to be permanently present on the shaft.

After the intervention, the outer part can simply be removed again from the shaft and, depending on the design, can be separately cleaned and sterilized, or, if it is designed as a disposable part, can just be discarded.

The endoscope itself, without the outer part, can be subjected to the usual autoclaving processes. In contrast to the prior art mentioned at the outset, there is therefore no need to take the precaution of ensuring that the shaft is completely covered by the outer part. This opens up the possibility of providing the outer part with lateral openings or slits via which it can be mounted onto the shaft in a simple lateral application procedure.

The image transmission and lighting system is completely separate from the deflector mechanism, such that no connections or passages critical in terms of sealing have to be present between these structural elements.

In one embodiment of the invention, the shaft has a flexible area at the transition from the deflectable end portion to the shaft.

As has already been indicated, this measure has the advantage that this flexible area has to be present only in the area in which the deflection is to be effected.

In another embodiment of the invention, the flexible area has a resetting element by means of which the shaft and the distal end portion can be brought into a linear orientation.

This measure has the important handling advantage that, if no deflection is wanted, the deflector mechanism is simply released, and the resetting element brings this deflected area back to the rectilinear orientation.

This measure also has the advantage that, if the endoscope is used without the outer part, the resetting element ensures that the endoscope remains in the rectilinear orientation. The resetting element therefore ensures that, despite the flexible deflection site, the shaft body as a whole is a stiff, rigid body, unless it is acted upon by the deflecting force of the deflector mechanism. This greatly increases flexibility and also facilitates handling of the endoscope as a rigid endoscope.

In one embodiment of the invention, the resetting element is designed as a spring element.

This measure has the advantage that the resetting force is made available by this spring element, and such elements can be made from strong, in particular metal materials that withstand the harsh conditions. Thus, for example, the spring element can be a helical spring arranged around the outside of the shaft, specifically in the flexible area thereof. This not only provides the restoring force upon deflection, the spring at the same time represents a mechanical support for the flexible area. If, for example, the flexible area of the shaft was created by weakening the material of the shaft wall, the spring coiled around it contributes to the mechanical stability of this area.

In another embodiment of the invention, the shaft is rigid in the direction proximal from the flexible area.

Alternatively or in addition to this, the distal end portion can be rigid.

These measures have the advantage that, on one side of the deflection site, the shaft is designed as in a rigid endoscope, that is to say ensures the same mechanical protection of the lighting and image transmission systems housed therein and also allows the endoscope to be handled as a rigid endoscope. Rigid endoscopes in minimally invasive surgery are usually introduced into the body via a trocar, which is still possible with the endoscope according to the invention, despite its deflectability, in particular also when no outer part is mounted on it.

In another embodiment of the invention, the distal end portion has a greater diameter than the shaft.

A noticeable advantage is that the area of greater diameter provides more force application points for the deflector mechanism in order to deflect this area from the rectilinear direction. The outer part, which engages around the shaft in this deflectable and distal end portion, is then accordingly provided with a greater diameter, such that a sufficient number of points of application are present outside the axis of symmetry in order to effect a deflection, for example by means of a tensile force, on the other side of the axis of symmetry. A further advantage is that the distal end portion of greater diameter can be slid completely through the trocar such that, along the shaft portion of smaller diameter present in the trocar, there is sufficient space available thereafter for guiding further instruments through the trocar.

In another embodiment of the invention, the shaft has, at the proximal end, a portion of greater diameter.

This measure has the advantage that this proximal end area of greater diameter makes handling easier and functions basically as a kind of grip via which the assembly composed of shaft and of outer part can be handled. This also makes the mounting or detachment of the two parts easier, especially if the endoscope concerned is a thin endoscope.

In another embodiment of the invention, the outer part is designed as a shell-like element at least partially open at the side.

This measure has the advantage that the shell-like element can be mounted on the shaft in a simple lateral application movement, if appropriate also combined with a subsequent axial displacement. At the same time, such a shell-like element is sufficiently stable to support the deflector mechanism and also to take up the deflecting forces and overcome the resistance forces of the deflectable distal end portion of the shaft.

In another embodiment, the lateral opening is designed as a longitudinal slit via which the shaft can be laterally clipped into place.

This measure has the advantage that this longitudinal slit represents an orientation aid that helps the operator assemble the shaft and outer part.

In another embodiment of the invention, areas of greater diameter are present at the proximal and distal ends of the outer part, and the areas of greater diameter on the shaft can be engaged with a form fit in said areas of the outer part.

These measures have the advantage that the shaft and outer part are assembled, particularly at these proximal and distal ends, very securely and across a large surface area.

In another embodiment of the invention, the areas of greater diameter of the shaft can be slid axially into the areas of greater diameter of the outer part.

This measure has the advantage that the outer part can first of all be mounted laterally in a slightly axially offset state, and, by means of axial relative displacement, the areas of greater diameter of the shaft can then penetrate axially into the corresponding portions of greater diameter of the outer part. The lateral slit can be dimensioned such that the areas of greater diameter of the shaft cannot escape laterally from the slit in the areas of greater diameter of the outer part. This therefore at the same time represents a means of securing the shaft against falling out.

As has already been mentioned, endoscopes in minimally invasive surgery are introduced into the body, for example into the abdomen, via trocars. To enlarge the inner cavities, they are inflated with a gas, in most cases $CO_2$. Consequently, in order to avoid escapes of gas, an endoscope has to be inserted as far as possible in a gas-tight manner through the trocar and into the cavity in the body.

The areas of greater diameter can be chosen such that their external diameters correspond approximately to the clear internal diameter of the trocar, as a result of which a gas-tight closure can be achieved.

When tile endoscope is used, at least its proximal widened area corresponds to the trocar. If the assembly of shaft and outer part is inserted, the widened area of the outer part corresponds to the trocar.

In another embodiment of the invention, a central longitudinal axis of the distal end portion of the outer part is laterally offset in relation to the central longitudinal axis of a central portion of the outer part.

It has already been noted that the assembly of endoscope and outer part can be introduced like a rigid endoscope through a trocar and into the body. The lateral freedom of movement of the deflector mechanism is then limited by the clear internal diameter of the trocar at least in the area in which the endoscope is received in the trocar. The deflection of the distal end portion of course only takes place when it has been pushed through the trocar and into the body cavity, while a relatively long axial portion of the endoscope remains in the inside of the trocar, which limits the lateral movements.

This asymmetrical or non-coaxial arrangement permits force application points lying on the other side of the central longitudinal axis of symmetry, in order to bring about the deflection.

In another embodiment of the invention, the lateral offset is such that the central portion and the distal end portion have at least a common surface line.

This measure has the considerable advantage that a relatively large lateral offset is possible, that is to say points of application lying on the other side of the axis of symmetry are available for the deflector mechanism, while the common centre line however ensures exact guiding of the outer part on the inside wall of the trocar during introduction into the body.

This also greatly facilitates the handling of the endoscope.

In one embodiment of the invention, the deflector mechanism is designed in such a way that it can deflect a distal portion of the outer part in which the distal deflectable end portion of the shaft is housed.

This measure has the advantage that the outer part can be made stable, and its distal portion, which receives the distal passively deflectable end portion of the shaft, can be deflected via the mechanism. This contributes as a whole to the stability and secure handling of the assembly during the deflection.

In another embodiment of the invention, the deflector mechanism has an actuating element that extends from distal to proximal and that is connected at the distal end to the deflectable portion of the outer part and at the proximal end to a pivot lever.

This measure has the advantage that the elongate actuating element permits a slender design, and, as has already been mentioned, the assembly can be inserted into the body and handled via a trocar, the pivot lever at the proximal end being easy for the operator to grip and actuate, which makes handling much simpler.

In another embodiment, the outer part is designed as a disposable part, e.g. as a plastic part.

By means of the aforementioned simple mechanical configuration, it is possible to design the outer part as an inexpensive disposable part, such that it does not have to be cleaned and sterilized.

In another embodiment of the invention, an imaging system of the image transmission system is housed in the deflectable distal end portion of the shaft.

This measure has the advantage that the endoscope can be designed as a video endoscope and the imaging system is securely housed and protected in the deflectable distal end portion.

In another embodiment of the invention, the imaging system has at least one electronic image sensor with a lens.

This measure has the advantage that the image can be focussed onto the sensor via the lens, such that an excellent image can be generated, these structural parts being accommodated and protected in the deflectable distal end portion of the shaft. Suitable image sensors are miniature CCDs or CMOS sensors with suitable pixel resolution.

In another embodiment of the invention, a sensor is present which, by the effect of gravitation, makes a position or "up" direction detectable.

This measure has the advantage that this position can be indicated to the operator via this sensor, for example if he deflects the distal end portion inside the body and rotates the endoscope about its longitudinal axis.

In another embodiment of the invention, a micromotor arranged in the distal end portion of the shaft is coupled to the image sensor and rotates this about its image sensor axis.

This measure has the advantage that, by means of the rotation, the image can be returned to a defined orientation, for example an upright orientation, that helps the operator.

In another embodiment of the invention, the micromotor can be controlled via a control unit which, using the information from the position sensor, rotates the image sensor in such a way that, after deflection of the distal end portion, the image information can be brought into a respectively similar orientation on a monitor.

As has already been mentioned, this measure has the advantage of orientation for the operator, the particular advantage being that this can be controlled via the control unit and also automated.

These structural parts can be mechanically protected in the deflectable end portion and hermetically closed off from the outside, such that only cables, which carry the corresponding impulses, signals, light and the like, need to be routed through the deflection site and through the shaft to the proximal end. These cables can also be integrated sealingly into the inside face of the shaft in the deflectable area of the shaft, in order to ensure absolute leaktightness in this critical location and also to ensure additional mechanical protection.

This contributes in particular to such an endoscope being able to undergo frequent use/cleaning/autoclaving cycles, while nevertheless retaining a completely reliable function.

It will be appreciated that the aforementioned features and those still to be explained below can be used not only in the cited combinations but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which:

FIG. 3 shows a side view of the endoscope from Fig, 1, FIG. 4 shows a view corresponding to the view in FIG. 3, with the distal end portion deflected, and additionally shows a control unit and a monitor that are connected to the endoscope, FIG. 5 shows a greatly enlarged view of the shaft of the endoscope, partially in longitudinal section in the distal area, FIG. 6 shows a cross section along the line VI-VI, and FIG. 7 shows a cross-sectional view comparable to the cross-sectional view in FIG. 6, but with the outer part mounted on the shaft.

DETAILED DESCRIPTION OF PREFERRED EMBODIMENTS

Figure 1:
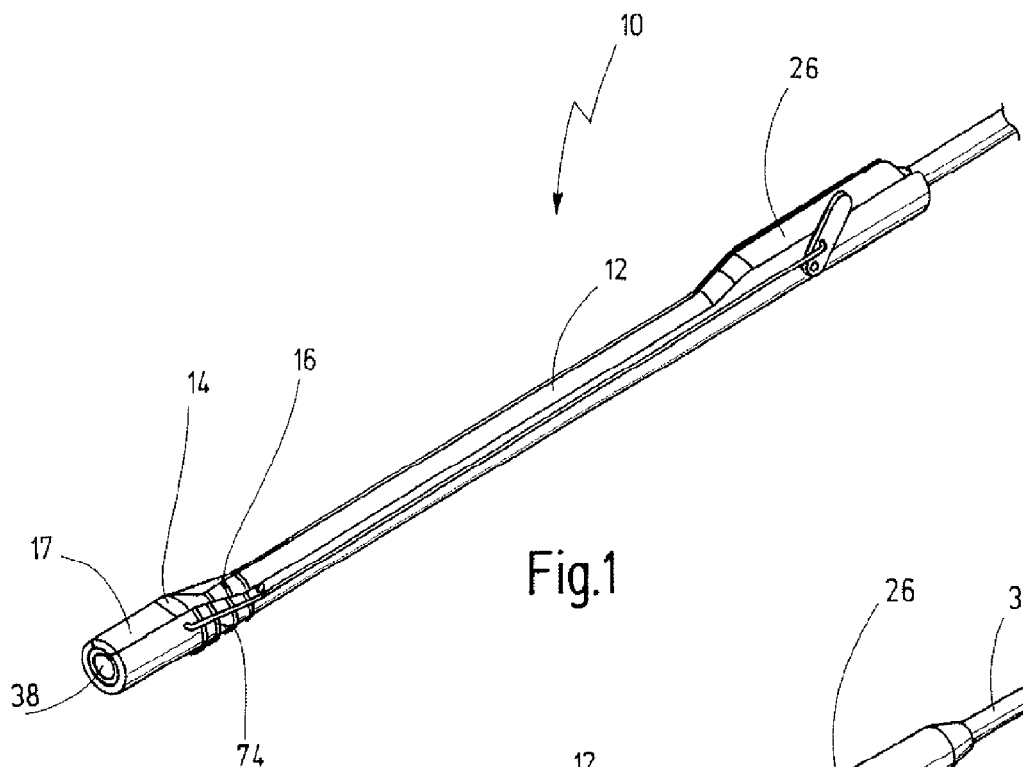
FIG. 1 shows a perspective view of an endoscope according to the invention, i.e. with an outer part mounted on the endoscope shaft.

An endoscope shown in the figures is designated overall by the reference number 10.

The endoscope 10 has an elongate, rectilinear stiff shaft 12, which has a distal end portion 14.

The transition from the shaft 12 to the distal end portion 14 comprises a flexible area 16. This is obtained by a relative thinning of the material of the shaft wall in this area. In this area, a resetting element 18 in the form of a helical spring 20 is placed around the shaft 12. Formed on the outside of the distal end portion 14 there is an attachment 17 which, as can be seen in particular from FIG. 6, has an approximately dovetail-shaped contour.

As will be seen in particular from the view in FIG. 5, the external diameter 22 of the shaft 12 is smaller than tire external diameter 24 of the distal end portion 14.

As will also be seen from FIG. 5, the shaft 12 has a proximal portion 26 whose external diameter 28 is likewise greater than the external diameter 22 of the shaft and corresponds approximately to the external diameter 24 of the distal end portion 14. A cable 30, whose purpose and function are explained later, issues from the proximal end of the proximal portion 26.

As will be seen in particular from the cross-sectional view in FIG. 5, the shaft has an outer sleeve 32 and, spaced slightly apart from the latter, an inner sleeve 34. Optical fibres 36 arranged in the annular space between outer sleeve 32 and inner sleeve 34 guide light from a light source (not shown here) from the proximal end to the distal output end for the light, as is of course customary in the construction of rigid endoscopes. The distal end portion 14 is sealed off hermetically at the distal end by a disc 38. Arranged on the inside face of the disc 38 there is what is called an optics cartridge 40, i.e. a lens. These therefore represent structural elements of an imaging system 41. Another structural part of the imaging system is formed by an image sensor 42 which, for example, is composed of a CCD chip that converts light into electrical signals.

The image sensor 42 is connected to a micromotor 46, which can rotate the image sensor 42 about the chip axis 43 thereof. A sensor 44 is also present, designed as a position sensor which, by the effect of gravitation, detects the "up" position or direction for example. This sensor 44 can also be arranged at another location of the shaft.

All these electronic structural parts are brought together with their corresponding leads to form an overall cable 30, which is routed through the inside of the shaft 12 as far as the proximal end and, as can be seen from FIG. 4 for example, can be led there to a control unit 50 that generates an image 54 on a monitor 52. These structural parts thus together represent the image transmission system, which is housed for the most part in the shaft.

Returning to FIGS. 1 and 2, it will be seen that an outer part 60 can be mounted on the shaft 12.

The outer part 60 is composed of an elongate shell 62 that has a lateral slit 64. A distal portion 66 of the shell 62 has, in the area of the slit, an opening 38 whose width is such that the dovetail-shaped attachment 17 of the distal end portion 14 of the shaft 12 can be received therein. This can be seen in particular by going from FIG. 6 to FIG. 7 or by going from FIG. 2 to FIG. 1.

The shell 62 further comprises a central portion 70 that serves to receive the central area of smaller diameter of the shaft 12.

The shell 62 accordingly has a proximal portion 72 that is designed such that the proximal portion 26 of the shaft 12 can be received therein.

The width of the slit 64 in the shell 62 can be designed such that the shaft 12 can be laterally pressed or clipped into the outer part 60 via the slit 64, if appropriate with slight widening of the latter.

The dovetail-shaped attachment 17 at the distal end portion 14 of the shaft 12 then ensures an exactly oriented fit that prevents relative rotations.

It is also possible for the slit 64 to be made slightly wider in the area of the central portion 70, such that the shaft 12 is first of all placed axially offset onto the shell 62 and then, by axial displacement, the portions 26 and 14 of greater diameter of the shaft 12 is pushed axially into the corresponding portions 66 and 72 of greater diameter of the outer part 60. This final fit is shown in FIG. 1, and the sliding movements are symbolized in FIG. 2 by the arrow 75.

Figure 2:
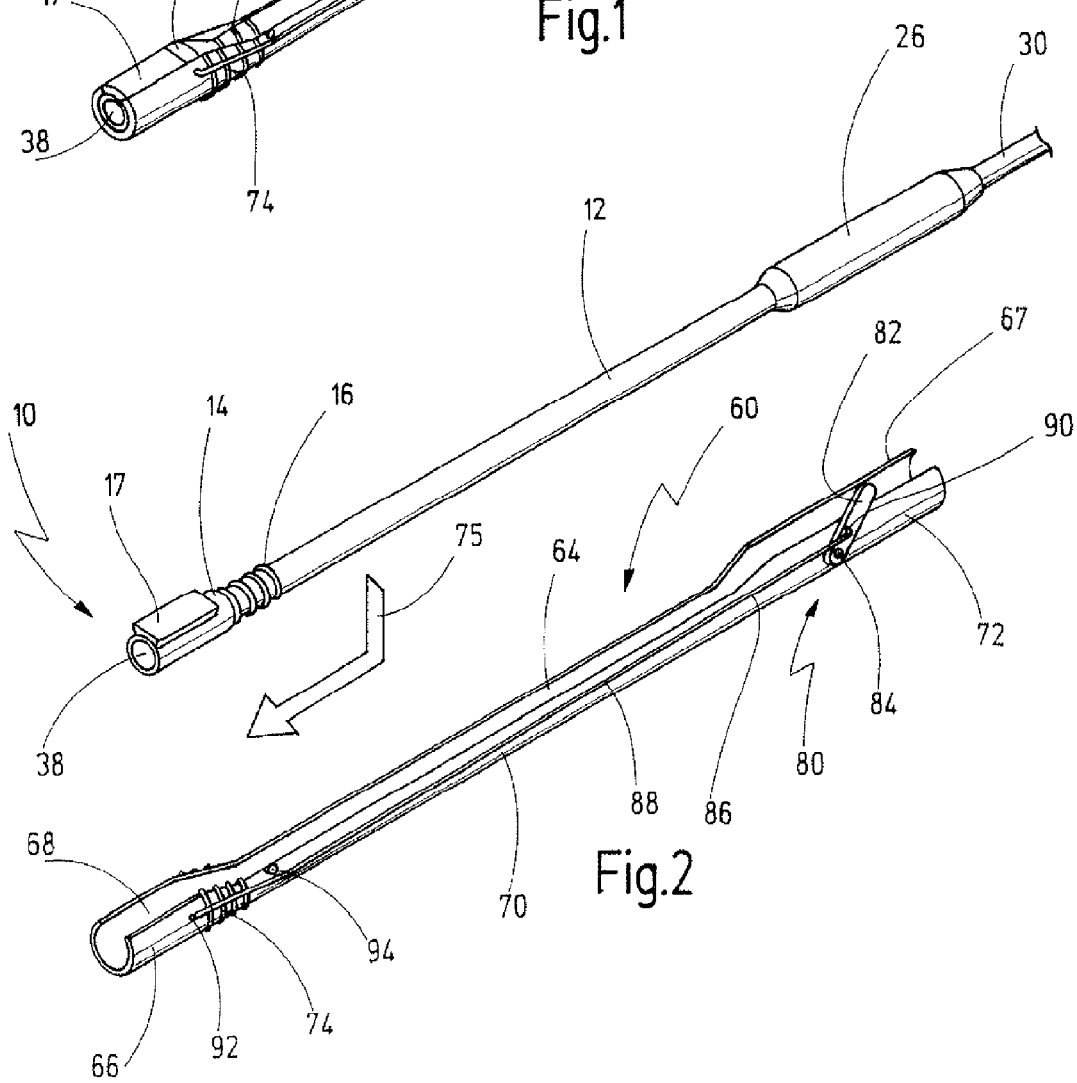
FIG. 2 shows a perspective exploded view, which is comparable to the view in FIG. 1 and in which the outer part is removed from the shaft.

As will be seen in particular from the views in FIGS. 2 and 3, the central longitudinal axis 67 of the distal portion 66 of the outer part 60 is laterally offset in relation to the central longitudinal axis 71 of the central portion 70.

The same applies to the proximal portion 72 of the shell 62 of the outer part 60.

The offset is such that these three portions 66, 70 and 72 have at least one common surface line 76.

This permits exact guiding on a cylindrical inner wall of a trocar via which the endoscope 10 is pushed into a body.

A deflector mechanism 80 is arranged on the outside of the shell 62 of the outer part 60.

The deflector mechanism 80 comprises a lever 82 in the form of a bracket that is arranged pivotably on the outer face of the proximal portion 72 of the shell 62 via a journal 84. An actuating element 86 in the form of an elongate wire 88 is secured at a distance from the pivot axis of the journal 84. A proximal end 90 of the wire 88 is inserted through an opening (not shown here) in the lever 82 and held fixedly thereon.

The distal end 92 of the wire 88 is secured on the outer face of the distal portion 66 of the shell 62.

The wire 88 is also guided around a diversion journal 94 which lies at a slight proximal distance from a flexible area 74 of the otherwise stiff shell 62. The flexible area 74 is composed of accordion-like folds of the material of the shell 62. The geometry of the points of articulation of journal 84 and wire 88 is chosen such that, if the lever is pivoted from the position shown in FIG. 3 to the position shown in FIG. 4, as is indicated by an arrow 89, the distal portion 66 of the shell 62 is pivoted in the same direction, as is indicated by the arrow 91 in FIG. 4.

This choice of geometry makes handling easier in the sense that the operator knows, when he pivots the lever 82 in this direction, that the distal portion 66 of the outer part is also pivoted in the same direction.

The distal end portion 14 of the shaft 12 is also pivoted in the same direction by this pivoting movement, since this distal end portion 14 is of course pushed into the distal portion 66 of the outer part 60. This therefore also results in the distal end portion 14 of the shaft 12 being deflected at the same time, but passively.

This is also made possible by provision of the flexible area 16 on the shaft 12.

The lever geometry is also chosen such that, when the lever 82 has been moved to the position shown in FIG. 4, the system is self-locking, i.e. it does not automatically return to the position shown in FIG. 3.

The geometry can also be chosen such that the lever 82 returns from the position shown in FIG. 4 to the position shown in FIG. 3, this resetting being promoted by the spring 20 that is placed around the flexible area 16 of the shaft 12.

It is therefore possible here to respond flexibly to the wishes of the operator and to produce suitable configurations.

In practical use, the shaft 12 and distal end portion 14 and also the corresponding distal portion and parts of the central portion 70 of the outer art 60 come to lie inside a trocar through which the endoscope 10 is inserted into a body during an intervention.

The lever 82 protrudes proximally from the trocar, such that the operator can actuate it.

When the endoscope in the position shown in FIG. 4, i.e. in the deflected position, is now rotated about its longitudinal axis, the image 54 on the monitor 52 also rotates correspondingly.

If it is desired that the image 54 always remains in the same orientation, for example that the subtense of the image 54 shown here by way of example as a triangle always comes to lie on the bottom edge of the monitor 52, this can be achieved through the aforementioned rotatability of the image sensor 42 via the micromotor 46. The gravitation or position sensor 44 allows the image sensor 42 to be set to the desired uniform orientation.

This can be controlled via the control unit 50 or can also be programmed, i.e. run automatically, depending on what is required. In FIGS. 1 and 2, the deflector mechanism 80 is arranged on one side of the shell 62 of the outer part 60.

Provision is also made for a second deflector mechanism 80' to be provided in mirror symmetry, as is indicated by the corresponding lever 82' in FIG. 3, or as can be seen from the view in FIG. 7.

The geometry of articulation of the deflector mechanism 80' can be chosen, for example, such that this deflector mechanism can be used to effect the move from the deflected position shown in FIG. 4 to the rectilinear orientation shown in FIG. 3.

Provision can also be made so that this deflector mechanism 80' acts in the same direction, only having from the outset another initial position of the lever 82', for example because the operation is desired in this way.

As will be seen in particular from FIG. 5, the shaft 12 of the endoscope 10 is always held in this rectilinear orientation by the spring 20 placed around the flexible area 16, unless it is acted upon by outer deflecting forces, for example by the outer part 60. In the illustrative embodiment shown, the shaft is flexible only in the area of the flexible area 16, otherwise it is stiff.

The shaft 12 or endoscope 10 can thus also be used without an attached outer part 60, in other words as a "classical" rigid endoscope, if so desired.

When the distal end portion 14 is pushed through the trocar into the body, there is sufficient space in the trocar, along the smaller-diameter portion of the shaft 12, for other instruments to be guided in and through. This in particular shows the versatility of the endoscope 10 according to the invention.

What is claimed is:

1. An endoscope, comprising:
    a shaft housing a lighting and an image transmission system,
    said shaft being entirely made of metal and having a stiff proximal end portion, a stiff distal end portion and having a flexible area, said stiff proximal end portion extending along a majority of a length of said shaft,
    said flexible area extending between said stiff proximal end portion and said stiff distal end portion, said flexible area being more flexible than said stiff proximal end portion and said stiff distal end portion, said flexible area allowing said stiff distal end portion to deflect relative to said stiff proximal end portion,
    a resetting element being fixedly placed at said flexible area,
    said resetting element comprises a spring which fixedly surrounds said flexible area of said shaft,
    said resetting element permanently urges said stiff distal end portion into a linear alignment with said stiff proximal end portion of said shaft, and
    an outer part, the outer part being attached to said shaft by being releasably mounted laterally onto said shaft,
    said outer part being a stiff single piece shell having a flexible area at a location where said flexible area of said shaft is located when said outer part is mounted to said shaft, a stiff distal end of said shell housing said stiff distal end portion of said shaft,
    said outer part having a deflector mechanism for deflecting said stiff distal end of said shell together with said stiff distal end portion of said shaft against a force of said resetting element.

2. The endoscope of claim 1, wherein said shaft is rigid in a direction proximal from said flexible area.

3. The endoscope of claim 1, wherein said distal end portion has a diameter which is greater than a diameter of said stiff proximal end portion and said flexible area of said shaft.

4. The endoscope of claim 1, wherein said shaft has, at a proximal end, a portion of enlarged diameter.

5. The endoscope of claim 1, wherein said outer part is designed as a shell-like element at least partially open at a side.

6. The endoscope of claim 5, wherein said outer part has a lateral opening designed as a longitudinal slit via which said slit and said shaft are laterally clipped into place.

7. The endoscope of claim 3, wherein areas of an enlarged diameter are present at a proximal and a distal end of said outer part, and said portions of said shaft having a greater diameter and an enlarged portion are engaged with said areas of said outer part.

8. The endoscope of claim 7, wherein said portions of said shaft having a greater diameter and an enlarged portion are slid axially into said areas of enlarged diameter of said outer part.

9. The endoscope of claim 8, wherein a central longitudinal axis of a distal portion of said outer part is laterally offset in relation to a central longitudinal axis of a central portion of said outer part.

10. The endoscope of claim 9, wherein said lateral offset is such that said central portion and said distal end portion of said outer part have at least a common surface line.

11. The endoscope of claim 1, wherein said deflector mechanism is designed in such a way that it can deflect a distal portion of said outer part in which said stiff distal end portion of said shaft is received.

12. The endoscope of claim 11, wherein said deflector mechanism has an actuating element that extends from said distal end to a proximal end of said outer part and which is connected at a distal end thereof to a deflectable portion of said outer part and at a proximal end thereof to a pivot lever.

13. The endoscope of claim 1, wherein said outer part is designed as a disposable part.

14. The endoscope of claim 1, wherein an imaging system of said image transmission system is housed in said deflectable distal end portion of said shaft.

15. The endoscope of claim 14, wherein said imaging system has an image sensor with a lens.

16. The endoscope of claim 15, further comprising a sensor, the sensor, by an effect of gravitation, detects a position of the endoscope.

17. An endoscope of claim 16, wherein a micromotor is arranged in said distal end portion of said shaft and is coupled to said image sensor and rotates about an image sensor axis.

18. The endoscope of claim 17, wherein said micromotor is controlled via control units, using an information from said sensor, rotates said image sensor in such a way, that, after a deflection of said distal end portion of said shaft, an image information on a monitor is brought into a respectively similar orientation.

19. The endoscope of claim 4, wherein areas of an enlarged diameter are present at a proximal and said distal end of said outer part, and said greater diameter and said enlarged portion of said shaft are engaged with areas of said outer part.

20. The endoscope of claim 1, wherein said outer part has a lateral opening designed as a longitudinal slit extending along an entire length of said outer part.

* * * * *